US00PP36728P2

(12) United States Plant Patent
Grosser

(10) Patent No.: US PP36,728 P2
(45) Date of Patent: Jun. 10, 2025

(54) MANDARIN PLANT NAMED 'N40W-5-1'

(50) Latin Name: ***Citrus* sp.**
Varietal Denomination: N40W-5-1

(71) Applicant: Florida Foundation Seed Producers, Inc., Marianna, FL (US)

(72) Inventor: Jude Grosser, Winter Haven, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 18/369,705

(22) Filed: Sep. 18, 2023

(51) Int. Cl.
*A01H 5/08* (2018.01)
*A01H 6/78* (2018.01)

(52) U.S. Cl.
USPC ..... Plt./201
CPC ..... *A01H 6/785* (2018.05)

(58) Field of Classification Search
USPC ..... Plt./156, 201
See application file for complete search history.

(56) References Cited

U.S. PATENT DOCUMENTS

PP27,744 P3 3/2017 Grosser
PP29,091 P3 3/2018 Grosser
PP36,088 P2 * 9/2024 Grosser ..... A01H 6/785 Plt./201

OTHER PUBLICATIONS

The Citrus Budwood Annual Report 2018-2019 (Florida Department of Agriculture and Consumer Services) (https://ccmedia.fdacs.gov/content/download/89339/file/2018-2019-Annual-Report-Citrus-Budwood.pdf)(p. 1-2, and 14)(total pp. 3) (Retrieved from the Internet May 13, 2024).*

* cited by examiner

*Primary Examiner* — Susan McCormick Ewoldt
*Assistant Examiner* — Zachariah Allan Kay
(74) *Attorney, Agent, or Firm* — Koenig IP Works, PLLC; Katherine Koenig

(57) ABSTRACT

A new and distinct cultivar of *Citrus* plant named 'N40W-5-1', characterized by small to medium, nearly seedless fruit with a unique and robust sweet flavor; compact growth habit; flavorful juice; and fragrant fruit with a smooth rind. The new *Citrus* cultivar also is more tolerant to HLB than most mandarin varieties, especially when trees are supplemented with controlled release fertilizer (CRF) containing an enhanced micronutrient package.

10 Drawing Sheets

Genus and species: *Citrus* sp.
Cultivar denomination: 'N40W-5-1'.

CROSS-REFERENCE TO RELATED APPLICATIONS

N/A.

ACKNOWLEDGEMENT OF FEDERAL RESEARCH SUPPORT

N/A.

BACKGROUND OF THE NEW CULTIVAR

The present invention relates to a new and distinct cultivar of *Citrus*, botanically known as *Citrus* sp. and hereinafter referred to by the name 'N40W-5-1'.

The new *Citrus* cultivar 'N40W-5-1' was selected from a population of 50 plants grown from irradiated budwood (using cobalt 60, Vindicator Co., Mulberry Florida) from a seedy mandarin hybrid ('Snack'; not patented) of unknown parentage. The original parent is believed to be a nucellar seedling (diploid) of 'Nova' mandarin hybrid of Clementine mandarin (*Citrus clementina* or *Citrus reticulata*) x Orlando tangelo (Duncan grapefruit, *Citrus paradisi* x Dancy tangerine, *Citrus reticulata*) (none patented). A simple sequence repeats (SSR) marker analysis conducted in Gainesville, Florida, supports this supposition. The original 'N40W-5-1' tree was planted in far west block of a growing facility in Gainesville, Florida, in 2004, and was grafted to 'Swingle' citrumelo (not patented) rootstock. True-to-typeness of the new cultivar was demonstrated by grafting six additional trees of 'N40W-5-1' onto rootstock of a different variety, 'UFR-3' (U.S. Plant Pat. No. 27,744), which were planted in Gainesville, Florida, in Fall of 2016.

Plant Breeder's Rights for this cultivar have not been applied for. The new *Citrus* cultivar 'N40W-5-1' has not been made publicly available more than one year prior to the filing of this application.

SUMMARY

The new *Citrus* cultivar 'N40W-5-1' has not been observed under all possible environmental conditions. The phenotype of the new cultivar may vary with variations in environment and cultural practices such as temperature, light intensity, fertilization, irrigation, and application of plant growth regulators without any change in genotype.

The new *Citrus* cultivar 'N40W-5-1' produces a small to medium, nearly seedless fruit with a unique and robust sweet flavor. In some situations, 'N40W-5-1' may replace the previously released sister selection 'N40W-6-3' (sold commercially as Seedless Snack; U.S. Plant Pat. No. 29,091), that has exhibited a severe granulation problem since HLB (Haunglongbing or *Citrus* greening disease) has become endemic in Florida. Fruit on trees of 'N40W-5-1' grown adjacent to trees of the problematic 'N40W-6-3' have produced large crops of fruit with no granulation the past two seasons, whereas approximately 80% of fruit from 'N40W-6-3' was granulated and unacceptable for the market (for example, as shown in FIG. 11). Fruit of 'N40W-5-1' also typically has a smoother rind than fruit of 'N40W-6-3'. Harvest can begin in October, but the fruit reaches maximum flavor and quality around Thanksgiving. The fruit generally has a minimal amount of seeds, averaging two small seeds per fruit, unlike the original selection of 'Snack' that averages more than 16 seeds per fruit. However, this precludes using the name Seedless Snack, as the 'N40W-6-3' selection referred to as Seedless Snack averages less than one seed per fruit. Juice obtained from fruit of 'N40W-5-1' also has outstanding flavor. Fruit of 'N40W-5-1' has a unique, pleasant fragrance, suggesting potential value for the peel oil. Further, 'N40W-5-1' makes small compact trees when grown on 'Swingle' citrumelo or 'UFR-3' rootstocks. The new cultivar is suited for sale as a fresh market *Citrus* fruit.

DESCRIPTION OF THE FIGURES

The accompanying photographs (as shown in FIGS. 1-11) illustrate the overall appearance of the new *Citrus* cultivar 'N40W-5-1'. These photographs show the colors as true as can be reasonably obtained in colored reproductions of this type. Colors in the photographs may differ slightly from the color values cited in the detailed botanical description, which accurately describe the colors of the new *Citrus* cultivar.

DETAILED BOTANICAL DESCRIPTION OF THE CULTIVAR

Figure 1:
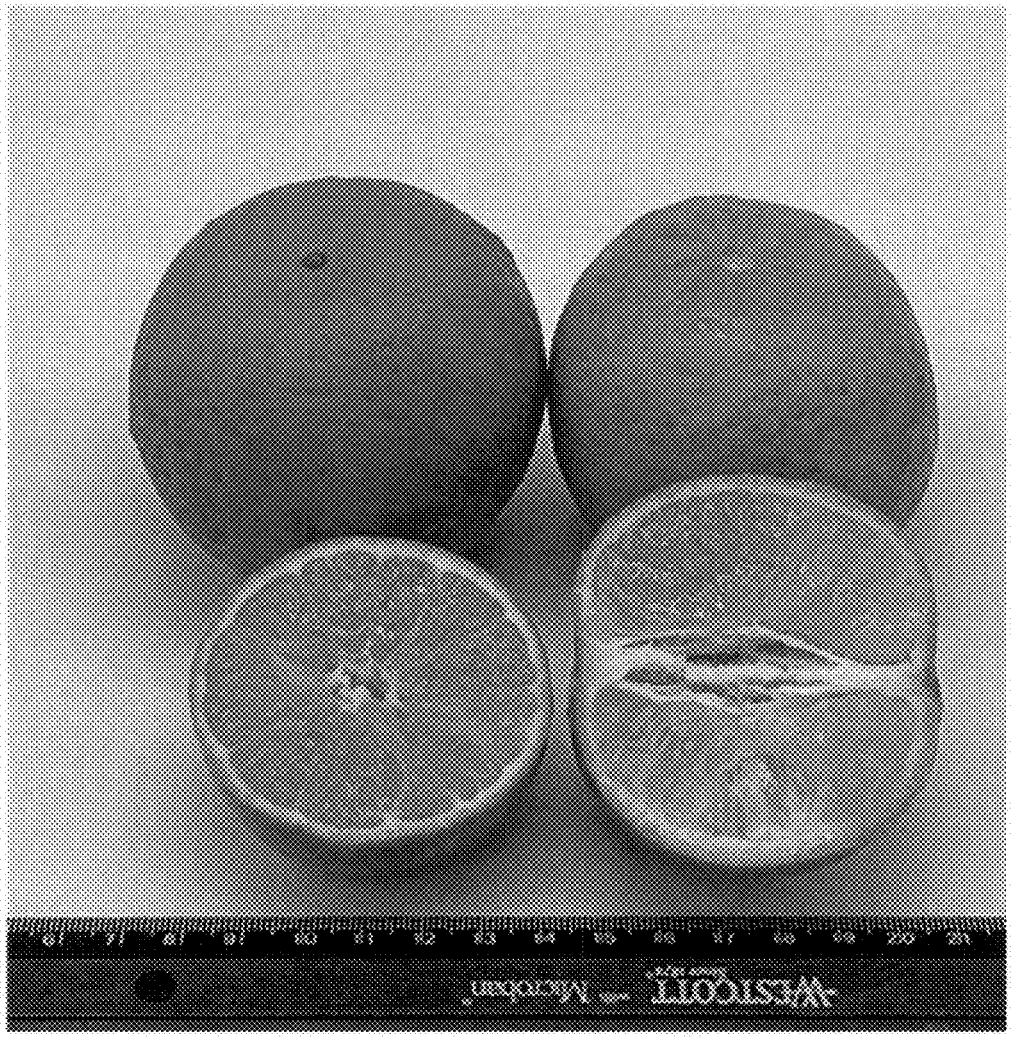
FIGS. 1 and 2 show whole and cut fruit of the new *Citrus* cultivar 'N40W-5-1' as shown and described herein.
Figure 2:
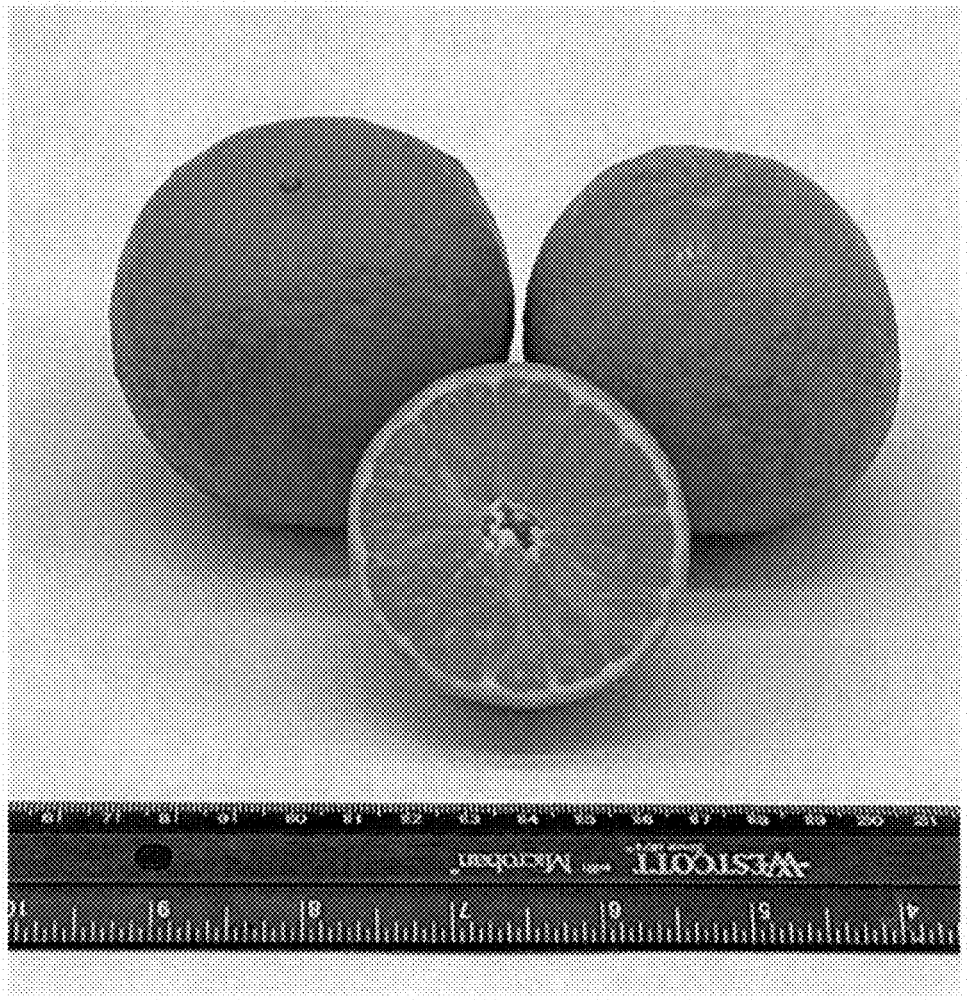
Figure 3:
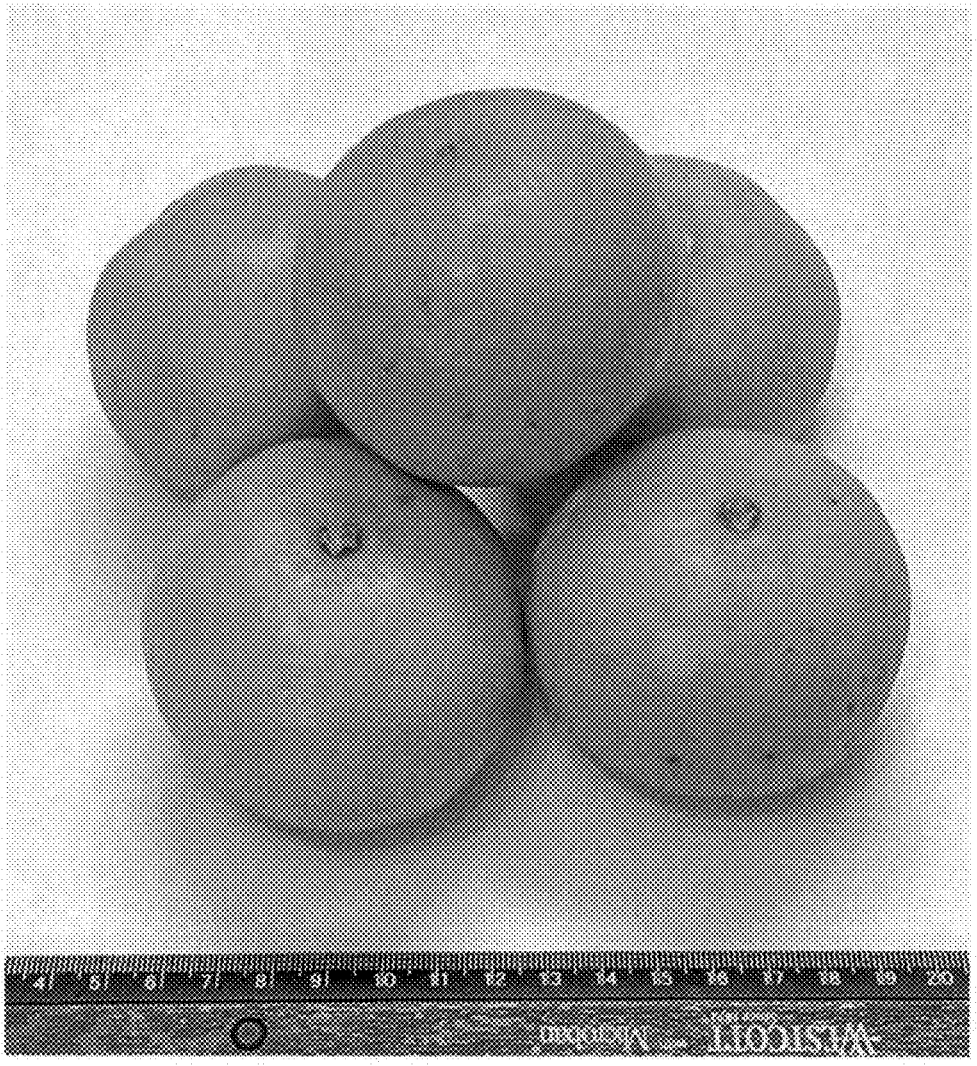
FIG. 3 shows whole fruit of the new *Citrus* cultivar.
Figure 4:
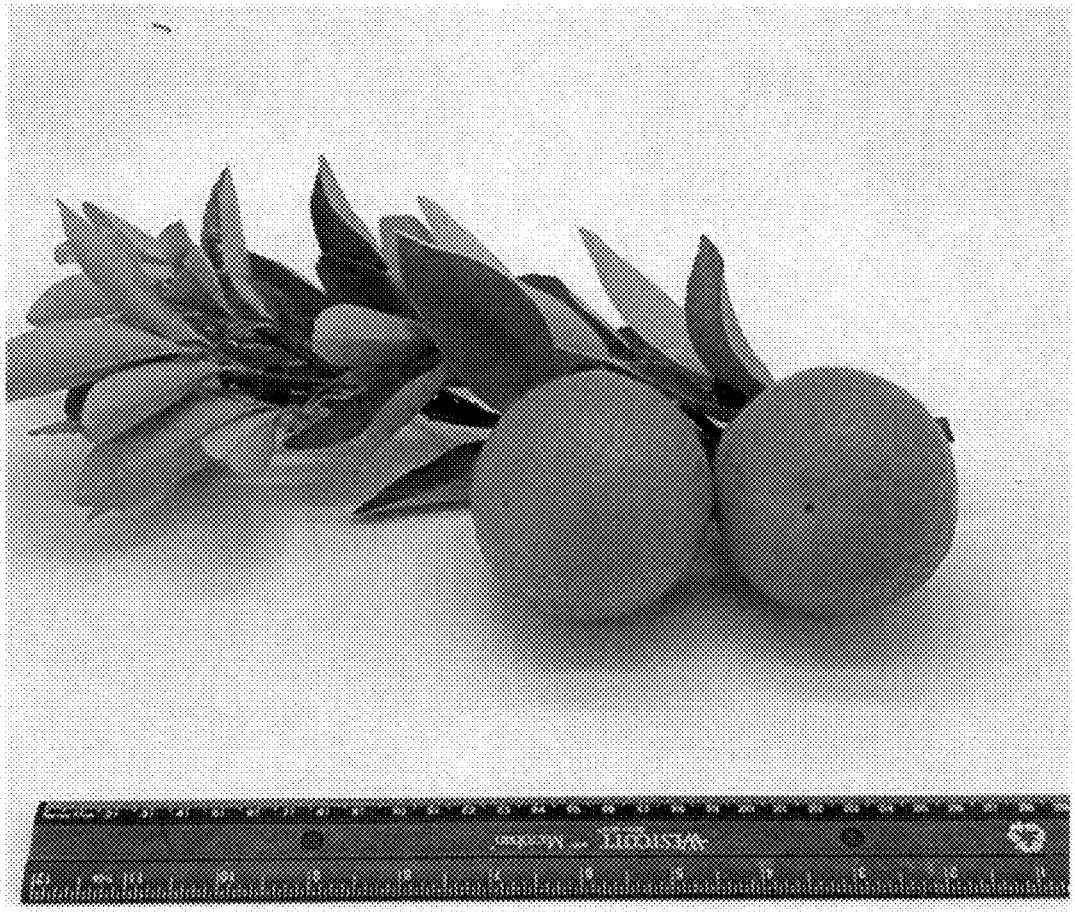
FIG. 4 shows whole fruit and cut foliage of the new *Citrus* cultivar.
Figure 5:
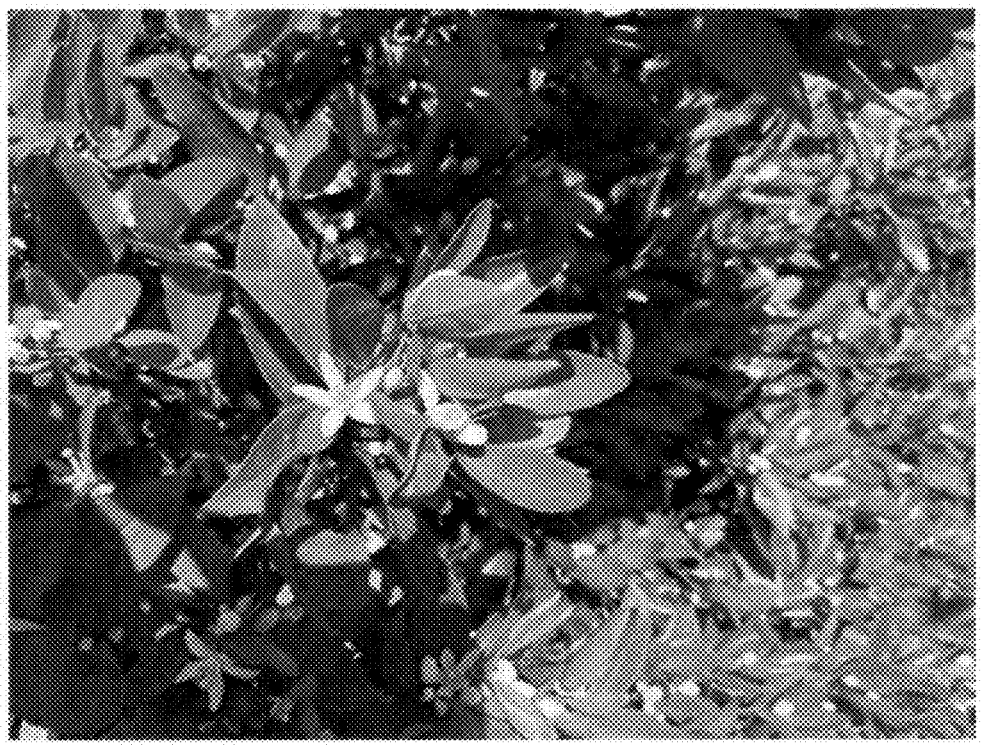
FIG. 5 shows flowers and foliage of the new *Citrus* cultivar.
Figure 6:
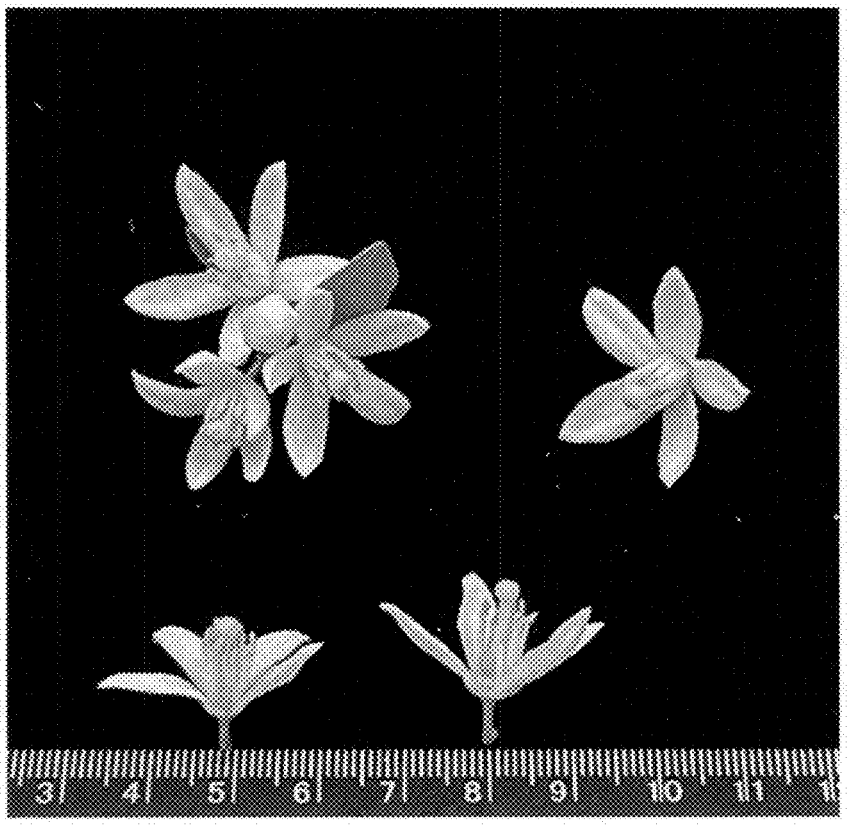
FIG. 6 shows a close-up view of flowers of the new *Citrus* cultivar.
Figure 7:
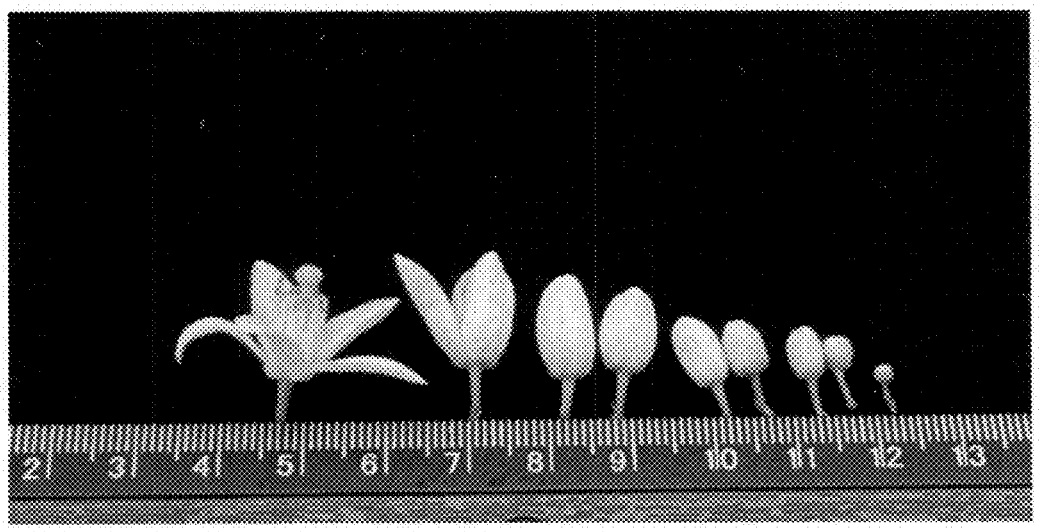
FIG. 7 shows a close-up view of mature and immature flowers of the new *Citrus* cultivar.
Figure 8:
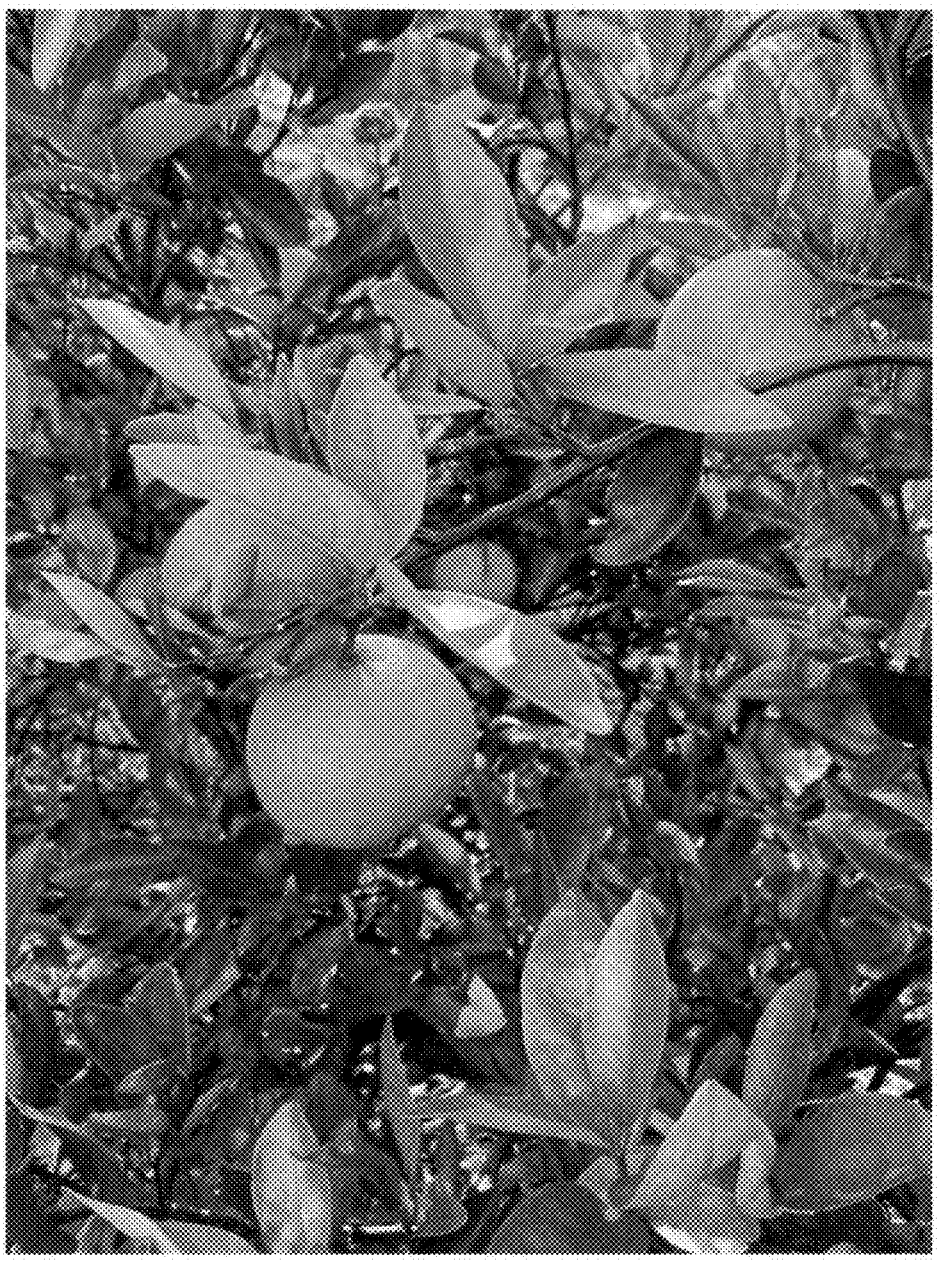
FIG. 8 shows fruit on a branch of the new *Citrus* cultivar.
Figure 9:
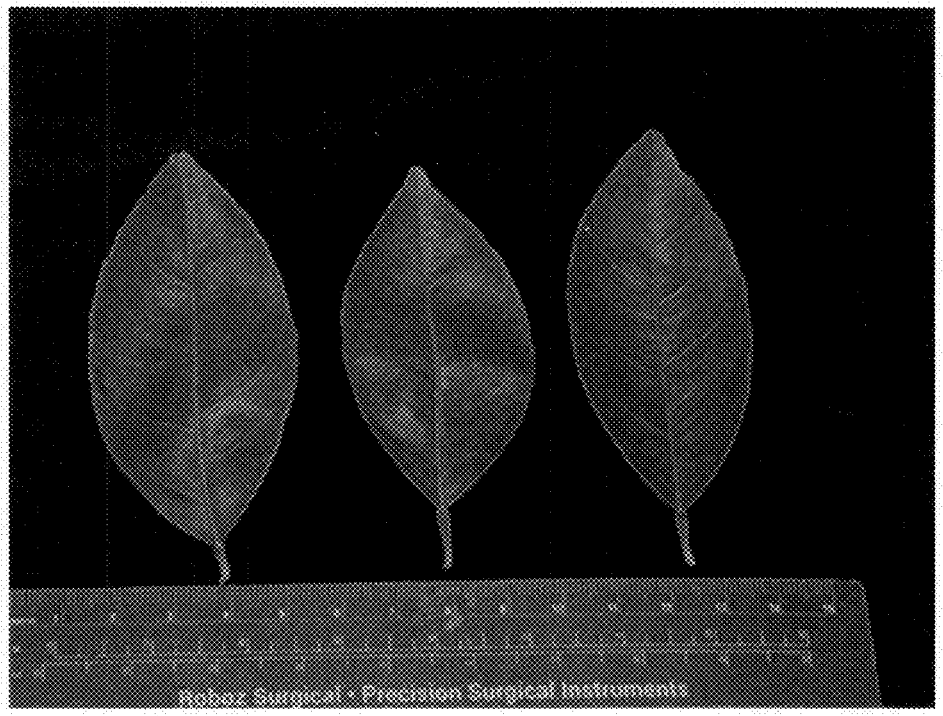
FIG. 9 shows a close-up view of leaves of the new *Citrus* cultivar.
Figure 10:
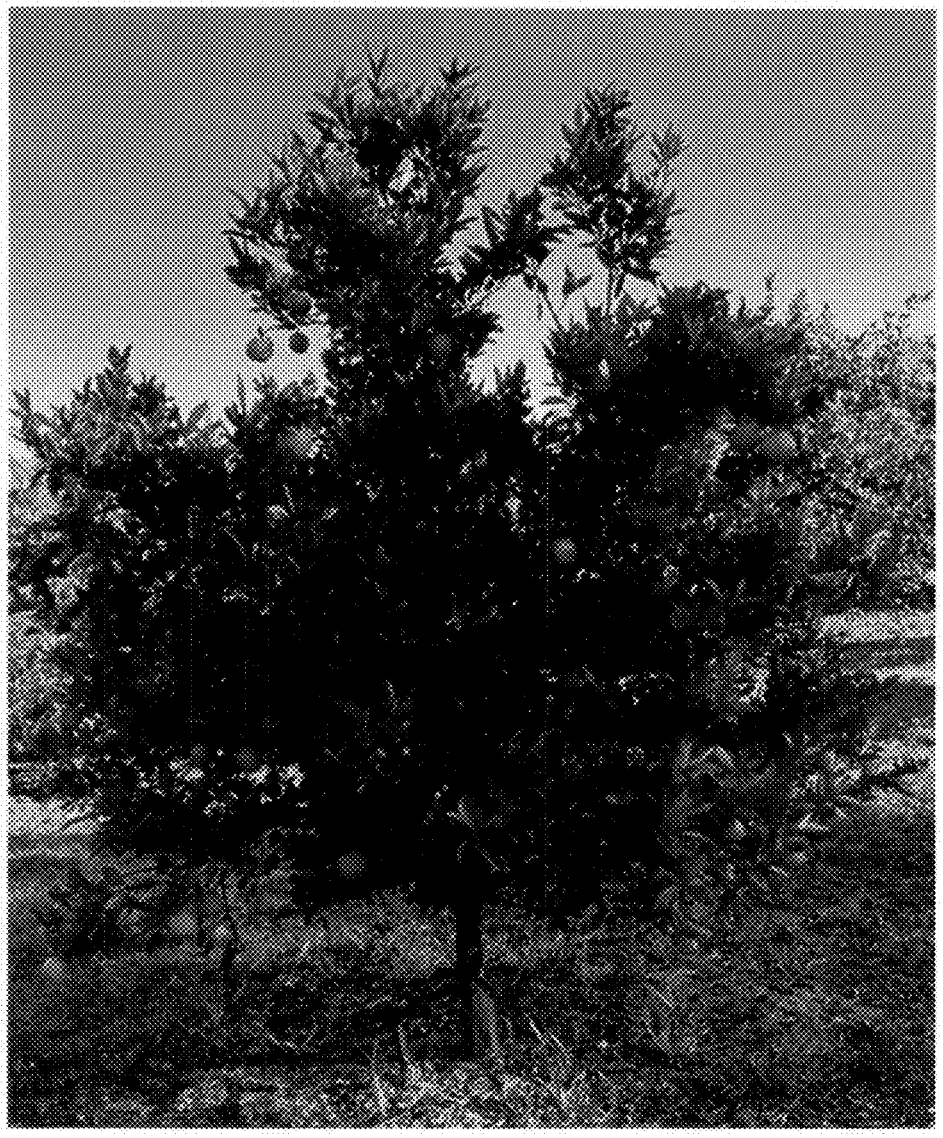
FIG. 10 shows the overall plant growth habit in an 8-year-old tree of the new *Citrus* cultivar.
Figure 11:
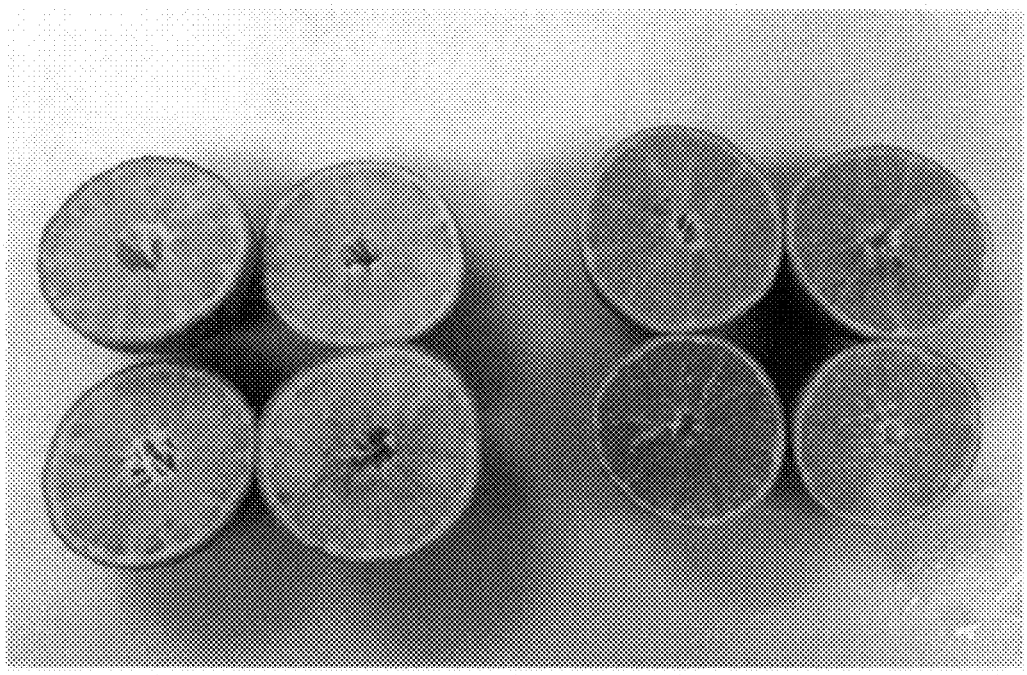
FIG. 11 shows a comparison of cut fruit of the cultivar 'N40W-6-3' (left) with cut fruit of the new cultivar 'N40W-5-1' (right) after exposure of the trees to *Citrus* greening disease, with severe granulation being visible in fruit of 'N40W-6-3' as a result.

The following detailed description of the new *Citrus* variety 'N40W-5-1' was obtained using a 4-5 year-old tree growing on 'UFR-3' rootstock in Lake Alfred, Florida, growing in well-drained sands and soil with poor organic content. The tree was growing under subtropical growing conditions, with hot, humid, and rainy summers (June through August) and mild but variable weather the rest of the year, and generally with a few mild freezes. Leaf and flower data was collected in March, and mature fruit data was collected in November. The colors (except those in common terms) are described from R.H.S. Colour Chart published by The Royal Horticultural Society in London (Second Edition), in association with the Flower Council of Holland.

BOTANICAL DESCRIPTION

Botanical classification:

*Family*.—Rutaceae.

*Botanical name*.—*Citrus* sp.

*Common name*.—Mandarin.

*Cultivar*.—'N40W-5-1'.

Parentage: The new *Citrus* cultivar is derived via budwood irradiation, and is believed to be a nucellar seeding (diploid) of 'Nova' mandarin hybrid of Clementine mandarin (*Citrus clementina* or *Citrus reticulata*) x Orlando tangelo (Duncan grapefruit, *Citrus paradisi* x Dancy tangerine, *Citrus reticulata*) (none patented).

Propagation: Field trees were propagated using standard *Citrus* nursery techniques. Rootstock liners were grown from nucellar seed, and the scion was grafted onto the rootstock using the standard inverted "T" graft method.

Tree description:

*Ploidy*.—Diploid.

*Size*.—Medium. Width across row: 2.3 meters. Width down row: 2.1 meters.

*Tree height*.—2.5 meters.

*Tree canopy diameter*.—2.6 meters.

*Vigor*.—Low to moderate.

*Density*.—Canopies are moderately dense.

*Tree shape* (*form*).—Oblate shape.

*Growth habit* (*current season*).—Vegetative growth mostly upright, with some lateral growth.

Trunk:

*Trunk diameter*.—6.7 cm at 30 cm above the ground.

*Trunk texture*.—Relatively smooth.

*Trunk bark color*.—RHS N199B (Grey-Brown Group).

Branches:

*Branch length*.—2.4 meters on average.

*Branch diameter*.—5.1 cm on average.

*Crotch angle*.—Acute, being 80-85 degrees on average (less than 90 degrees) in the middle of the tree, while some on the outside of the tree are obtuse, being 100-105 degrees on average (more than 90 degrees).

*Branch texture*.—Medium rough.

*Branch color*.—RHS 199A (Grey-Brown Group).

Foliage description:

*Size* (*lamina average*).—Length: 85 mm on average. Width: 40 mm on average. Length to width (L:W) ratio: 2:1 on average.

*Thickness*.—Relatively thick.

*Type*.—Simple (unifoliate).

*Shape*.—Elliptical. Apex: Retuse. Base: Acute.

*Margin*.—Dented with a split end.

*Surface*.—Upper surface: Smooth. Lower surface: Medium venation, with veins being pinnately netted.

*Color*.—Upper (adaxial) surface: RHS N137A (Green Group). Lower (abaxial) surface: RHS 138B (Green Group).

*Petiole*.—Shape and attachment: Brevipetiolate; shorter than leaf lamina. Junction between petiole and lamina is articulate. Shape (petiole wing): Obovate with narrow end at the base. Length: 9.5 mm on average. Width: 3 mm on average. Color: RHS N137D (Green Group).

Inflorescence description:

*Flower type*.—Hermaphrodite.

*Flower bearing*.—Single or cluster. Branches have flowers grown in cluster, and each cluster consists of 3-6 flowers. Individual flowers grow from leaf terminals and leaf axillaries.

*Flower diameter*.—Fully open flower with average diameter of 24 mm.

*Flower depth*.—18 mm on average.

*Flower blooming period*.—Generally March, but depends on weather patterns. First bloom: Late February. Full bloom: March.

*Fragrance*.—Fragrant.

*Flower bud size*.—Length, initial visible flower bud: 1.6 mm on average. Length, mature buds before opening: 22 mm on average. Diameter, initial visible flower bud: 1.2 mm on average. Diameter, mature bud before opening: 5.3 mm on average.

*Flower bud shape, initial visible flower bud*.—Round dome shape.

*Flower bud shape, mature flower bud*.—Elongated olive shape.

*Flower bud color*.—Initial visible flower bud: RHS 144A (Yellow Green Group). Mature bud: RHS NN155D (White Group).

*Fertility*.—Appears to be self-fertile.

*Petals*.—Number (per flower): 5. Petal length: 16 mm on average. Petal width: 5.1 mm on average. Petal shape: Flat spatula shape. Apex shape: Smooth with obtuse angle. Base shape: Obtuse: Color: Upper surface: RHS NN155D (White Group). Lower surface: RHS NN155D (White Group). Margin: Smooth.

*Sepals*.—Number (per flower): 5. Shape: Delta-shaped with acute angle at the apex; however, some have a flat angle at the apex. Length: 4 mm on average. Width: 2.5 mm on average. Apex shape: Acute angle at apex; however, some have a flat angle at the apex. Margin: Smooth. Color: Upper surface: RHS 158A (Green White Group). Lower surface: RHS 157D (green white).

*Pedicel*.—Length: 10 mm on average. Diameter: 1 mm on average. Color: RHS 144B (Yellow Green Group).

*Stamen*.—Number (per flower): 21 on average. Length: 12 mm on average.

*Anther*.—Length: 2.5 mm on average. Width: 0.7 mm on average. Color: RHS 14C (Yellow Orange Group). Pollen color (general): RHS 13A (Yellow Group).

*Pistil*.—Number (per flower): 1. Length: 12 mm on average. Color: RHS 153A (Yellow Green Group). Style length: 9.5 mm on average. Style diameter: 1.5 mm on average. Style color: RHS 144B (Yellow Group). Ovary shape: Oval shape. Ovary diameter: 3 mm on average.

Fruit:

*Size*.—Uniform, small to medium in size.

*Average weight* (*per individual fruit*).—200 grams.

*Length* (*height*).—7 cm on average.

*Diameter*.—6.9 cm on average.

*Shape*.—Spherical, earthy.

*Shape* (*cross section*).—Round.

*Apex*.—Round.

*Base*.—Round.

*Harvest*.—Date of first pick: Late October in Florida. Date of last pick: Mid-December in Florida.

*Fruit stem*.—Length: 11 mm on average. Diameter: 4 mm on average. Color: RHS N199B (Greyed-Brown Group).

*Rind*.—Adherence: Medium-strong to weak adherence of albedo (mesocarp) to flesh (endocarp) and medium adherence of albedo to peel. Thickness: Thin; 3-4 mm on average. Texture: Medium firm with excellent flavor. Surface texture: Medium smooth. Color: Flavedo (epicarp): RHS 25B (Orange Group). Albedo (mesocarp): RHS 155A (White-Yellow Group). Style end: Closed. Rind oil cell density: 110-155 cell/square cm. Oil gland size: Big; 0.8 mm on average.

*Flesh*.—Number of segments: 12 on average. Segment wall thickness: Thin to medium-soft, but of sufficient strength to maintain integrity as separated. Segment length: 6.4 cm on average. Segment width: 2.6 cm on average.

*Juice*.—Presence: Abundant. Color: RHS 25B (Orange Group). Texture: Soft to medium. Vesicles: Length: 12 mm on average. Diameter (thickness): 3 mm on average. Juice quality: Brix: 14.5-15. Acidity (average): 0.9%. Ratio: 16.11-16.7. Juice color: 37.5 (*Citrus* Index Number). Lb. solid/box: Not available.

*Seeds*.—1-3 seeds per fruit, with an average of 2 seeds per fruit in trees with cross pollination.

Resistance to disease: Susceptible to HLB (Huanglongbing), but more tolerant than most mandarin varieties, especially when trees are supplemented with controlled release fertilizer (CRF) containing an enhanced micronutrient package. No other disease issues have been observed (including *Citrus* canker or *Alternaria* spp.).

Fruit productivity rating (scale of 1-5 with 1 being very poor fruit production and 5 being maximum fruit production, in comparison to other commercial varieties): 'N40W-5-1' score is 3. The yield of 'N40W-5-1' is estimated to be between 2-3 90-lb. field boxes per tee at ages 6-8. However, yields of plants of 'N40W-5-1' that are infected with HLB are significantly less when grown on current commercial rootstocks. No formal yield data is available.

HLB disease index rating (scale of 1-5 with 1 being very poor health, near death, and 5 being completely healthy, in comparison to other commercial varieties): The score of 'N40W-5-1' is 3.5.

COMPARISON WITH KNOWN CULTIVARS

The new *Citrus* cultivar 'N40W-5-1' can be distinguished from the commercial variety 'Nova' (unpatented) in that fruit of 'Nova' are generally quite seedy under Central Florida growing conditions, where cross pollination from oranges and grapefruit happens regularly. In contrast, fruit of 'N40W-5-1' generally has 1-3 seeds per fruit, regardless of cross pollination. Additionally, fruit of 'N40W-5-1' generally matures 2-3 weeks earlier than 'Nova' during most years. Further, 'Nova' often has a granulation issue in Florida, whereas 'N40W-5-1' does not.

What is claimed is:

1. A new and distinct variety of mandarin plant named 'N40W-5-1' as illustrated and described herein.

* * * * *